United States Patent
Elsen-Wahrer et al.

(10) Patent No.: US 10,398,635 B1
(45) Date of Patent: *Sep. 3, 2019

(54) COMPOSITIONS AND METHODS FOR IMPROVING COLOR DEPOSIT AND DURABILITY OF COLOR IN ARTIFICIALLY COLORED HAIR

(71) Applicant: L'OREAL, Paris (FR)

(72) Inventors: Andrea Elsen-Wahrer, Linden, NJ (US); Jim Singer, South Orange, NJ (US); Jeffrey Wang, Jersey City, NJ (US); Lisa Jablonski, Edison, NJ (US); Martin Asare, Springfield, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/940,148

(22) Filed: Mar. 29, 2018

(51) Int. Cl.
*A61Q 5/10* (2006.01)
*A61K 8/49* (2006.01)
*A61K 8/365* (2006.01)
*A61K 8/20* (2006.01)
*A61K 8/22* (2006.01)

(52) U.S. Cl.
CPC .............. *A61K 8/4973* (2013.01); *A61K 8/20* (2013.01); *A61K 8/22* (2013.01); *A61K 8/365* (2013.01); *A61Q 5/10* (2013.01); *A61K 2800/43* (2013.01); *A61K 2800/882* (2013.01)

(58) Field of Classification Search
CPC ... A61Q 5/10; A61K 8/20; A61K 8/22; A61K 8/365; A61K 8/46; A61K 2800/43; A61K 2800/882
See application file for complete search history.

(56) References Cited

U.S. PATENT DOCUMENTS

| | | | |
|---|---|---|---|
| 5,961,667 A * | 10/1999 | Doehling | A61Q 5/10 8/406 |
| 2010/0192969 A1 * | 8/2010 | DeGeorge | A61K 8/19 132/208 |
| 2012/0121737 A1 | 5/2012 | Vielhaber et al. | |
| 2013/0219633 A1 * | 8/2013 | Sabelle | A61K 8/347 8/424 |
| 2013/0344018 A1 | 12/2013 | Fack et al. | |
| 2017/0151169 A1 | 6/2017 | Scheunemann et al. | |

FOREIGN PATENT DOCUMENTS

| | | | |
|---|---|---|---|
| EP | 1889603 A2 | 2/2008 | |
| EP | 1915981 A1 | 4/2008 | |
| WO | WO2012/175720 A1 * | 12/2012 | ............ A61Q 5/10 |
| WO | WO-2017/197099 A1 | 11/2017 | |
| WO | WO-2019/046389 A1 | 3/2019 | |
| WO | WO-2019/046396 A1 | 3/2019 | |

OTHER PUBLICATIONS

International Search Report and Written Opinion dated Jun. 18, 2019 for corresponding PCT Application No. PCT/US2019/023972.
"Intelligent Cell Renewal Cream", GNPD; Mintel, 2005 XP055593292.
"Magica CC Hair Care and Colour Multi-Tone Shine Mask", GNPD; Mintel, 2014 XP055593292.

* cited by examiner

*Primary Examiner* — Eisa B Elhilo
(74) *Attorney, Agent, or Firm* — Polsinelli PC (L'oreal USA)

(57) ABSTRACT

The present disclosure relates to hair coloring agents and compositions, and methods for improving the quality and durability of color in artificially colored hair. The compositions employ divalent metal salts of inorganic acids, monovalent or divalent metal salts of organic acids, antioxidants, and colorants. Methods are described wherein hair is contacted with the compositions of the present disclosure, resulting in improved artificial color deposition, as well as improved quality and durability of the color in artificially colored hair.

23 Claims, No Drawings

COMPOSITIONS AND METHODS FOR IMPROVING COLOR DEPOSIT AND DURABILITY OF COLOR IN ARTIFICIALLY COLORED HAIR

FIELD OF THE DISCLOSURE

The present disclosure relates to compositions and methods for depositing color and providing color protection to hair, in particular, for improving the quality and durability of color in artificially colored hair.

BACKGROUND

There are many products available for changing the natural color of hair. The process of changing the color of hair can involve either depositing an artificial color onto the hair, which provides a different shade or color to the hair, or lifting the color of the hair, such as for example, from a dark brown shade to a medium brown or a light brown shade. Hair color can be changed using permanent, semi-permanent, demi-permanent, or temporary hair coloring products.

Many consumers desire a permanent color change and therefore use products containing permanent dyes. Conventional permanent hair coloring products are dye compositions comprising oxidation dye precursors, which are also known as primary intermediates or couplers. These oxidation dye precursors are colorless or weakly colored compounds which, when combined with oxidizing products, give rise to colored complexes by a process of oxidative condensation. The oxidizing products conventionally use peroxides such as hydrogen peroxide as oxidizing agents. Such permanent hair color products also contain ammonia or other alkalizing agents such as monoethanolamine (MEA) which causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

Newly, permanently colored hair usually has a vibrant, shiny, and rich appearance. Unfortunately, however, in just a few short weeks, or in some cases even less, the color begins to fade due to washing, including shampooing, or exposure to environmental conditions. For instance, gorgeous rich brown colors become muddy and dull, beautiful shades of blonde turn brassy, and vibrant reds do not look so vibrant anymore acquiring golden, orange or brownish tonalities not desirable to the consumer. As described herein, the inventors of the instant disclosure have developed composition, methods and kits that improve color deposit onto hair and/or color durability by preventing color fading from hair.

SUMMARY OF THE DISCLOSURE

The present disclosure relates to improving the amount of artificial color deposited onto hair, as well as the quality and durability of the color in artificially colored hair (e.g., improving the fade resistance and the longevity of the color). The hair coloring agent, compositions, and methods described herein employ metal salts such as alkaline earth and alkali metal salts in combination with antioxidants in a hair dyeing system. The inventors discovered a surprising improvement in color quality and durability when alkaline earth metal salts, alkali metal salts and antioxidants are combined with a hair coloring or hair dyeing composition.

Antioxidants have long been used in coloring compositions, especially in hair coloring base compositions, which include oxidative dye precursors and optionally couplers. Historically, the purpose for including the antioxidants is to extend the shelf-life of coloring base compositions by preventing the oxidative dye precursors from becoming oxidized prematurely. The oxidative dye precursors must be preserved so they are available to penetrate the cuticle and cortex where the oxidation condensation reaction should occur. As hair coloring base compositions age, a percentage of the antioxidants deteriorate over time; the antioxidants deteriorate as they perform their anti-oxidizing action of donating electrons to neutralize free radicals.

The inventors discovered that treating or contacting hair with a combination of alkaline earth metal salts, alkali metal salts, and antioxidants and colorants improves the color quality and durability of the color in the hair. While not wishing to be bound by any particular theory, the inventors suspect that said combination function to prevent the oxidative dye precursors from reacting at the surface of the hair fibers. Once permanently lodged deep inside the hair fiber, the color is not easily removed. Therefore, the initial color quality and intensity that is achieved immediately upon artificially coloring the hair is maintained for longer periods of time.

In one aspect, the invention of the present disclosure is directed to a hair coloring agent comprising one or more compositions containing:
(a) one or more divalent metal salts of an inorganic acid;
(b) one or more monovalent or divalent metal salts of an organic acid;
(c) one or more antioxidants; and
(d) one or more colorants chosen from oxidative dye precursors, direct dyes, pigments, and mixtures thereof.

In another aspect, the invention of the present disclosure is directed to a hair coloring agent comprising:
(a) one or more divalent metal salts of an inorganic acid;
(b) one or more monovalent or divalent metal salts of an organic acid;
(c) one or more antioxidants; and
(d) one or more colorants chosen from oxidative dye precursors, direct dyes, pigments, and mixtures thereof;
wherein the one or more divalent metal salts of an inorganic acid, the one or more monovalent or divalent metal salts of an organic acid, and the one or more antioxidants are contained in a salt-antioxidant composition, and the one or more colorants chosen from oxidative dye precursors, direct dyes, pigments, and mixtures thereof are contained in a hair coloring or colorant composition; and
wherein the salt-antioxidant composition and hair coloring or colorant composition are to be combined before artificially coloring hair.

The hair coloring compositions and agents of the present disclosure are capable of being combined with one or more oxidizing agents or developer compositions containing one or more oxidizing agents in order to form ready to use dye compositions. The oxidizing agents are chosen from peroxides, persulfates, perborates, percarbonates, alkali metal bromates, ferricyanides, laccases, peroxidases, redox enzymes, their salts thereof, and mixtures thereof.

Methods for artificially coloring hair and/or inhibiting the artificial coloring from fading are also described, wherein said methods comprise contacting hair with the ready to use dye compositions for a sufficient period of time to achieve a desired color of the hair and/or alteration of the color of hair.

The one or more divalent metal salts of an inorganic acid are chosen from metal halides, metal hydroxides, metal sulfates, metal oxides, and mixtures thereof.

The one or more divalent metal salts of an inorganic acid or of an organic acid are chosen from salts of calcium, zinc, iron, nickel, copper, silver, magnesium, strontium, barium, manganese, cobalt, and mixtures thereof.

The one or more monovalent metal salts of an organic acid are chosen from salts of lithium, sodium, potassium, copper, silver, and mixtures thereof.

The organic acid of the one or more monovalent or divalent metal salts of an organic acid is chosen from C1 to C9 monocarboxylic or di-carboxylic acids, polycarboxylic acids, hydroxy-carboxylic acids, fatty acids having at least 10 carbon atoms, and organic acids with heterocyclic groups, for example, ascorbic acid, formic acid, acetic acid, glycolic acid, gluconic acid, lactic acid, mandelic acid, oxalic acid, maleic acid, malonic acid, glyoxylic acid, succinic acid, adipic acid, fumaric acid, sebacic acid, including citric acid, tartaric acid, malic acid, 2-hydroxy malonic acid, 2-hydroxyl n-butyl 1,2,4-tricarboxylic acid, glutaric acid, glucaric acid, 2-hydroxy n-butyl 1,3,4-tricarboxylic acid, pyrrolidone carboxylic acid, phenolsulfonic acid, and salicylic acid.

The antioxidants are chosen from ascorbic acid and its derivatives, sodium sulfite, sodium metabisulfite, sodium hydrosulfite, tocopherols, alpha-tocopherol, tocopheryl acetate, EDTA, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, Butylated hydroxytoluene (BHT), Butylated hydroxyanisole (BHA), N,N'-bis(3,4,5-trimethoxybenzyl)ethylenediamine and its salts, and mixtures thereof.

Finally, the instant disclosure relates to kits comprising the various compositions used to carry out the methods described herein. The kits may be used by hair-care professionals and salons for treating the hair of patrons or the kits may be purchased and used at home directly by consumers.

It is to be understood that both the foregoing general description and the following detailed description are exemplary and explanatory only, and are not restrictive of the disclosure.

Other subjects, characteristics, aspects and advantages of embodiments of the disclosure will emerge even more clearly on reading the description and the various examples that follow.

DETAILED DESCRIPTION OF THE DISCLOSURE

As used herein, the expression "one or more" means at least one and thus includes individual components as well as mixtures/combinations.

The terms "a," "an," and "the" are understood to encompass the plural as well as the singular.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%), such as within 9%, 8%, 7%, 6%, 5%, 4%, 3%, 2%, or 1%, according to various embodiments.

The term "comprising" (and its grammatical variations) as used herein is used in the inclusive sense of "having" or "including" or "containing" and not in the exclusive sense of "consisting only of".

As used herein, the terms "applying a composition onto hair" and all its grammatical variations, include "contacting hair with a composition" or "exposing hair to a composition" or "layering a composition onto hair" or "treating hair with a composition" with any suitable means, for example, by using the hands or fingers, or an applicator such as a brush or comb, or by spraying, or by delivering through a nozzle or bottle cap tip.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The terms "organic acid" mean compounds containing carbon atoms and hydrogen atoms and optionally heteroatoms such as S, O, N or P, alone or in combination.

When referring to "compositions described herein," all types of compositions are intended unless specifically described otherwise. The "compositions disclosed herein" include the compositions comprising one or more reducing agent, the composition comprising one or more lactones, to oxidizing compositions, etc.

The compositions and methods of the present disclosure can comprise, consist of, or consist essentially of the essential elements and limitations of the disclosure described herein, as well as any additional or optional ingredients, components, or limitations described herein or otherwise useful.

An embodiment of the present disclosure is directed to a hair coloring agent comprising one or more compositions containing:
(a) one or more divalent metal salts of an inorganic acid;
(b) one or more monovalent or divalent metal salts of an organic acid;
(c) one or more antioxidants; and
(d) one or more colorants chosen from oxidative dye precursors, direct dyes, pigments, and mixtures thereof.

In an embodiment, the one or more divalent metal salts of an inorganic acid, the one or more monovalent or divalent metal salts of an organic acid, and the one or more antioxidants are contained in a salt-antioxidant composition, and the one or more colorants chosen from oxidative dye precursors, direct dyes, pigments, and mixtures thereof are contained in a hair coloring or colorant composition such that the salt-antioxidant composition and hair coloring or colorant composition are combined in order to form the hair coloring agent before coloring hair.

In an embodiment, the one or more divalent metal salts of an inorganic acid are chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

In an embodiment, the one or more monovalent or divalent metal salts of an organic acid are chosen from metal ascorbates, formates, acetates, glycolates, gluconates, lactates, mandelates, oxalates, maleates, malonates, glyoxylates, succinates, adipates, fumarates, sebacates, citrates, tartarates, malates, tricarboxylates, glutarates, glucarates, pyrrolidone carboxylates, phenolsulfonate, salicylates, their salt derivatives thereof, salts of fatty acids having at least 10 carbon atoms, and mixtures thereof.

In an embodiment, the one or more divalent metal salts of an organic acid are chosen from zinc lactate, zinc gluconate, zinc phenolsulfonate, zinc salicylate, zinc pyrrolidone carboxylic acid (Zinc PCA), zinc citrate, zinc ascorbate, their salt derivatives thereof, and mixtures thereof.

In an embodiment, the one or more monovalent metal salts of an organic acid are chosen from sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof.

In an embodiment, the one or more monovalent metal salts of an organic acid includes a sodium salt and/or potassium salt.

In an embodiment, the hair coloring agent comprises one or more divalent metal salts of an inorganic acid chosen from calcium chloride, calcium sulfate, calcium nitrate, calcium carbonate and hydrogen carbonate, calcium phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof; and one or more divalent metal salts of an organic acid chosen from zinc lactate, zinc gluconate, zinc phenolsulfonate, zinc salicylate, zinc pyrrolidone carboxylic acid (Zinc PCA), zinc ascorbate, their derivatives thereof, and mixtures thereof.

In an embodiment, the hair coloring agent comprises one or more antioxidants chosen from ascorbic acid and its derivatives, sodium sulfite, sodium metabisulfite, sodium hydrosulfite, tocopherols, alpha-tocopherol, tocopheryl acetate, EDTA, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, Butylated hydroxytoluene (BHT), Butylated hydroxyanisole (BHA), N,N'-bis(3,4,5-trimethoxybenzyl)ethylenediamine and its salts, and mixtures thereof.

In an embodiment, the one or more divalent metal salts of an inorganic acid is chosen from calcium chloride, the one or more divalent metal salts of an organic acid is chosen from zinc gluconate. and the one or more antioxidants is chosen from ascorbic acid.

In various embodiments, the one or more compositions of the hair coloring agent such as the salt-antioxidant composition and the colorant or hair coloring composition contain a cosmetically acceptable solvent(s).

In an embodiment, the hair coloring compositions and agents of the present disclosure are capable of being combined with one or more oxidizing agents or developer compositions containing one or more oxidizing agents in order to form ready to use dye compositions. The oxidizing agents are chosen from peroxides, persulfates, perborates, percarbonates, alkali metal bromates, ferricyanides, laccases, peroxidases, redox enzymes, their salts thereof, and mixtures thereof.

In an embodiment, the hair coloring agent is formed from the combination of:
  a hair coloring composition comprising one or more colorants chosen from oxidative dye precursors, direct dyes, pigments, and mixtures thereof and a cosmetically acceptable solvent; and
  one or more divalent metal salts of an inorganic acid chosen from calcium chloride, calcium sulfate, calcium nitrate, calcium carbonate and hydrogen carbonate, calcium phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof;
  one or more monovalent or divalent metal salts of an organic acid chosen from zinc lactate, zinc gluconate, zinc phenolsulfonate, zinc salicylate, zinc pyrrolidone carboxylic acid (Zinc PCA), zinc ascorbate, their derivatives thereof, and mixtures thereof;
  one or more one or more antioxidants chosen from ascorbic acid and its derivatives, sodium sulfite, sodium metabisulfite, sodium hydrosulfite, tocopherols, alpha-tocopherol, tocopheryl acetate, EDTA, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, Butylated hydroxytoluene (BHT), Butylated hydroxyanisole (BHA), N,N'-bis(3,4,5-trimethoxybenzyl)ethylenediamine and its salts, and mixtures thereof;
  wherein the one or more divalent metal salts of an inorganic acid, the one or more monovalent or divalent metal salts of an organic acid, and the one or more antioxidants are provided as one or more separate components or as one component (composition) or as two components wherein one component comprises the metal salts and another component comprises the organic acids.

In an embodiment, the one or more separate components of metal salts and antioxidants are combined to form a salt-antioxidant composition which is then combined with the hair coloring composition, thereby forming the hair coloring agent.

In an embodiment, the salt-antioxidant composition comprises:
  at least 5 wt. %, or from about 5 wt. % to about 50% wt. %, or from about 7 wt. % to about 40% wt. %, or 10 wt. % to about 30% wt. % of the one or more divalent metal salts of an inorganic acid;
  at least 10 wt. %, or from about 10 wt. % to about 70% wt. %, or from about 20 wt. % to about 60% wt. %, or 30 wt. % to about 50% wt. % of the one or more monovalent or divalent metal salts of an organic acid; and
  at least 10 wt. %, or from about 10 wt. % to about 70% wt. %, or from about 20 wt. % to about 60% wt. %, or 30 wt. % to about 50% wt. % of the one or more antioxidants;
all weights being based on the total weight of the salt-antioxidant composition.

In embodiment, the hair coloring agent of the present disclosure comprises:
  from about 0.05 wt. % to about 10 wt. % or from about 0.1 wt. % to about 5 wt. % or from about 0.2 wt. % to about 3 wt. % including all ranges and sub-ranges therebetween, of the one or more divalent metal salts of an inorganic acid;
  from about 0.2 wt. % to about 20 wt. % or from about 0.2 wt. % to about 10 wt. % or from about 0.3 wt. % to about 5 wt. % including all ranges and sub-ranges therebetween, of the one or more monovalent or divalent metal salts of an organic acid; and from about 0.05 wt. % to about 10 wt. % or from about 0.1 wt. % to about 5 wt. %, or from about 0.2 wt. % to about 4 wt. %, or from about 0.3 wt. % to about 3 wt %, including all ranges and sub-ranges therebetween, of the one or more antioxidants;

one or more colorants chosen from oxidative dye precursors, direct dyes, pigments, and mixtures thereof; and a cosmetically acceptable solvent;

all weights being based on the total weight of the hair coloring agent composition.

In an embodiment, the hair coloring agent is capable of being mixed with an oxidizing composition (or developer composition) in order to form a ready to use hair dye composition wherein the oxidizing composition comprises: (i) one or more oxidizing agents chosen from peroxides, urea peroxide, alkali metal bromates, ferricyanides, peroxygenated salts, perborates, percarbonates, laccases, peroxidases, redox enzymes, and mixtures thereof; and (ii) a cosmetically acceptable solvent chosen from water and a water/organic solvent mixture.

In an embodiment, the hair coloring agent is a ready-to-use dye composition comprising:

from about 0.05 wt. % to about 5 wt. %, or from about 0.05 wt. % to about 4 wt %, or from about 0.1 wt. % to about 3 wt %, or from about 0.15 wt. % to about 3 wt %, including all ranges and sub-ranges therebetween, of the one or more divalent metal salts of an inorganic acid;

from about 0.2 wt. % to about 10 wt. %, or from about 0.3 wt. % to about 8 wt %, or from about 0.4 wt. % to about 5 wt %, or from about 0.5 wt. % to about 3 wt %, including all ranges and sub-ranges therebetween, of the one or more monovalent or divalent metal salts of an organic acid; and from about 0.05 wt. % to about 5 wt. % or from about 0.1 wt. % to about 5 wt. %, or from about 0.2 wt. % to about 4 wt. %, or from about 0.3 wt. % to about 3 wt %, or from about 0.2 wt. % to about 3 wt %, or from about 0.3 wt. % to about 2 wt %, or from about 0.4 wt. % to about 1 wt %, including all ranges and sub-ranges therebetween, of the one or more antioxidants;

one or more colorants chosen from oxidative dye precursors, direct dyes, pigments, and mixtures thereof;

one or more oxidizing agents; and a cosmetically acceptable solvent;

all weights being based on the total weight of the ready-to-use dye composition.

In an embodiment, the weight ratio of the one or more divalent metal salts of an inorganic acid to the one or more monovalent or divalent metal salts of an organic acid and to the one or more antioxidants in the ready to use hair dye composition is at about about (0.05-1):(0.1-5):(0.1-5) or at about (0.2-0.7):(0.2-4):(0.2-4) or at about (0.15-0.5):(0.5-3):(0.5-3).

In an embodiment, the one or more divalent metal salts of an inorganic acid are chosen from metal salts of halides, metal hydroxides, metal sulfates, metal oxides, and mixtures thereof, wherein the divalent metal is calcium, zinc, iron, nickel, copper, silver, magnesium, strontium, barium, manganese, or cobalt; the one or more monovalent or divalent metal salts of an organic acid are chosen from metal ascorbates, formates, acetates, glycolates, gluconates, lactates, mandelates, oxalates, maleates, malonates, glyoxylates, succinates, adipates, fumarates, sebacates, citrates, tartarates, malates, tricarboxylates, glutarates, glucarates, pyrrolidone carboxylates, phenolsulfonate, salicylates, their salt derivatives thereof, salts of fatty acids having at least 10 carbon atoms, and mixtures thereof; wherein the monovalent metal is lithium, sodium, potassium, copper, or silver; and wherein the divalent metal is calcium, zinc, iron, nickel, copper, silver, magnesium, strontium, barium, manganese, or cobalt; and the one or more antioxidants are chosen from ascorbic acid and its derivatives, sodium sulfite, sodium metabisulfite, sodium hydrosulfite, tocopherols, alpha-tocopherol, tocopheryl acetate, EDTA, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, Butylated hydroxytoluene (BHT), Butylated hydroxyanisole (BHA), N,N'-bis(3,4,5-trimethoxybenzyl)ethylenediamine and its salts, and mixtures thereof.

Ammonium salt compounds may be chosen from ammonium salts of halides (e.g., ammonium chloride), ammonium salts of sulfates (e.g., ammonium sulfate), and mixtures thereof.

Amino silicones may be chosen from silicones comprising at least one primary, secondary or tertiary amine or a quaternary ammonium group (i.e., a quaternized group).

Cationic surfactants may be chosen from optionally polyoxyalkylenated, primary, secondary or tertiary fatty amines, or salts thereof, and quaternary ammonium salts, and mixtures thereof.

The fatty amines generally comprise at least one C8-C30 hydrocarbon-based chain.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oleyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, hexadecyltrimethyl ammonium bromide, Quaternium-6 (PPG-9 Diethylmonium Chloride, a quaternary ammonium salt that conforms generally to a structural formula having an average value of 9 ethoxylation groups), and mixtures thereof.

The term "substantially free" or "essentially free" as used herein means that there is less than about 2% by weight of a specific material or ingredient added to a composition, based on the total weight of the compositions. The compositions of the disclosure may be free of the component(s) or may be "substantially free" or "essentially free" of the component(s) described for optional inclusion in said compositions. Nonetheless, the compositions may include less than 1 wt. %, or less than 0.5 wt. %, or less than 0.4 wt. %, or less than 0.3 wt. %, or less than 0.2 wt. %, or less than 0.1 wt. %, or less than 0.05 wt. % of the ingredient or material indicated.

In an embodiment, the hair coloring agent of the present disclosure comprises, in a cosmetically acceptable solvent:
(a) one or more divalent metal salts of an inorganic acid chosen from calcium chloride, calcium sulfate, calcium nitrate, calcium carbonate and hydrogen carbonate, calcium phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof;
(b) one or more monovalent or divalent metal salts of an organic acid chosen from zinc lactate, zinc gluconate, zinc phenolsulfonate, zinc salicylate, zinc pyrrolidone carboxylic acid (Zinc PCA), zinc ascorbate, sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof;
(c) one or more antioxidants chosen from ascorbic acid and its derivatives, sodium sulfite, sodium metabisulfite, sodium hydrosulfite, tocopherols, alpha-tocopherol, tocopheryl acetate, EDTA, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, Butylated hydroxytoluene (BHT), Butylated hydroxyanisole (BHA), N,N'-bis(3,4,5-trimethoxybenzyl)ethylenediamine and its salts, and mixtures thereof; and
(d) one or more colorants chosen from oxidative dye precursors, direct dyes, pigments, and mixtures thereof.

In an embodiment, the weight ratio of the one or more divalent metal salts of an inorganic acid to the one or more monovalent or divalent metal salts of an organic acid is from about 10:1 to about 1:10 or from about 8:1 to about 1:8 or from about 5:1 to about 1:5 or from about 3:1 to about 1:3 or from about 2:1 to about 1:2 or at about 1, including ranges and sub-ranges therebetween.

In an embodiment, the amount of the one or more divalent metal salts of an inorganic acid is greater than the amount of the one or more monovalent or divalent metal salts of an organic acid; for example, the weight ratio of the one or more divalent metal salts of an inorganic acid to the one or more monovalent or divalent metal salts of an organic acid can be 10:1, or 9:1, or 8:1, or 7:1, or 6:1, or 5:1, or 4;1, or 3;1, or 2:1.

In an embodiment, the amount of the one or more divalent metal salts of an inorganic acid is less than the amount of the one or more monovalent or divalent metal salts of an organic acid; for example, the weight ratio of the one or more divalent metal salts of an inorganic acid to the one or more monovalent or divalent metal salts of an organic acid can be 1:10, or 1:9, or 1:8, or 1:7, or 1:6, or 1:5, or 1:4, or 1:3, or 1:2.

In an embodiment, the weight ratio of the total amount of the one or more divalent metal salts of an inorganic acid and the one or more monovalent or divalent metal salts of an organic acid to the amount of the one or more antioxidants is from about 10:1 to about 1:10 or from about 8:1 to about 1:8 or from about 6:1 to about 1:6 or from about 4;1 to about 1:4, or from about 3:1 to about 1:3, or from about 2:1 to about 1:2, including ranges and sub-ranges therebetween.

In an embodiment, the weight ratio of the total amount of the one or more divalent metal salts of an inorganic acid and the one or more monovalent or divalent metal salts of an organic acid to the amount of the one or more antioxidants is at about 5;1, 4.5:1, 4:1, 3.5:1, 3:1, 2.5:1, 2:1, 1.91, 1.8:1, 1.7:1, 1.6;1, 1.5:1, 1.4:1, 1.3:1, 1.2:1, 1.1:1, 1:1, 1:0.8, 1:0.6, 1:0.5, 1:0.4, or 1:0.2.

It has now been surprisingly and unexpectedly discovered that the use of the compositions, methods, and kits of the present disclosure resulted in good deposit of artificial color onto hair as well as durable artificial color wherein the fading of the artificial was found to be minimal even over several shampooings of the hair.

Divalent Metal Salts of an Inorganic Acid

The one or more divalent metal salts of an inorganic acid may be chosen from metal halides, metal hydroxides, metal sulfates, metal oxides, and mixtures thereof.

The divalent metals with which the metal salts are formed are calcium, zinc, iron, nickel, copper, silver, magnesium, strontium, barium, manganese, cobalt, and mixtures thereof.

Suitable examples of the one or more divalent metal salts of an inorganic acid may be chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

In an embodiment, the one or more divalent metal salts of an inorganic acid includes a calcium salt.

In an embodiment, the calcium salt is calcium chloride.

The one or more divalent metal salts of an inorganic acid may be present in the salt-oxidation compositions and/or hair coloring agents and/or ready-to-use dye mixtures of the present disclosure in an amount of from above 0 wt. % to about 50 wt. % or from about 0.01 wt. % to about 30 wt. % or from about 0.05 wt. % to about 20 wt. % or from about 0.05 wt. % to about 15 wt. % or from about 0.05 wt. % to about 10 wt. % or from about 0.0.075 wt. % to about 8 wt. %, or from about 0.1 wt. % to about 5 wt. %, or from about 0.2 wt. % to about 3 wt. %, including all ranges and sub-ranges therebetween, based on the total weight of the salt-oxidation compositions and/or hair coloring agents and/ or ready-to-use dye mixtures.

In various embodiments, the one or more divalent metal salts of an inorganic acid is present in the salt-oxidation compositions of the present disclosure in a wt. % amount of about 0.05, 0.1, 0.15, 0.2, 0.3, 0.4, 0.5, 0.6, 0.7, 0.8, 0.9, 1, 1.5, 1.6, 1.7, 1.8, 1.9, 2, 2.5, 3, 3.5, 4, 4.5, 5, 5.5, 6, 6.5, 7, 7.5, 8, 8.2, 8.3, 8.4, 8.5, 8.6, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4. 12.5, 12.6, 12.7, 12.8, 12.9, 13, 13.2, 13.5, 13.7, 14, 14.2, 14.5, 14.7, 15, 15.5, 16, 16.5, 17, 17.5, 18, 18.5, 19, 19.5, or 20, based on the total weight of the salt-oxidation compositions.

In various embodiments, the one or more divalent metal salts of an inorganic acid is present in the hair coloring agents and/or ready-to-use dye mixtures of the present disclosure in a wt. % amount of about 0.01, 0.05, 0.1, 0.15, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, or 6.5, based on the total weight of the hair coloring agents and/or ready-to-use dye mixtures.

Monovalent or Divalent Metal Salts of an Organic Acid

The one or more monovalent or divalent metal salts of an organic acid may be chosen from metal salts wherein the organic acid is chosen from C1 to C9 monocarboxylic or di-carboxylic acids, polycarboxylic acids, hydroxy-carboxylic acids, and fatty acids having at least 10 carbon atoms including ascorbic acid, formic acid, acetic acid, glycolic acid, gluconic acid, lactic acid, mandelic acid, oxalic acid, maleic acid, malonic acid, glyoxylic acid, succinic acid, adipic acid, fumaric acid, sebacic acid, including citric acid, tartaric acid, malic acid, 2-hydroxy malonic acid, 2-hydroxyl n-butyl 1,2,4-tricarboxylic acid, glutaric acid, glucaric acid, 2-hydroxy n-butyl 1,3,4-tricarboxylic acid, pyrrolidone carboxylic acid, phenolsulfonic acid, and salicylic acid.

Suitable examples monovalent or divalent metal salts of an organic acid are chosen from metal ascorbates, formates, acetates, glycolates, gluconates, lactates, mandelates, oxalates, maleates, malonates, glyoxylates, succinates, adipates, fumarates, sebacates, citrates, tartarates, malates, tricarboxylates, glutarates, glucarates, pyrrolidone carboxylates, phenolsulfonate, salicylates, their salt derivatives thereof, salts of fatty acids having at least 10 carbon atoms, and mixtures thereof.

In an embodiment, the one or more divalent metal salts of an organic acid are chosen from zinc lactate, zinc gluconate, zinc phenolsulfonate, zinc salicylate, zinc pyrrolidone carboxylic acid (Zinc PCA), zinc ascorbate, zinc citrate, their salt derivatives thereof, and mixtures thereof.

In an embodiment, the one or more divalent metal salts of an organic acid includes a zinc salt.

In an embodiment, the zinc salt is zinc gluconate.

In an embodiment, the one or more monovalent metal salts of an organic acid are chosen from sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof.

In an embodiment, the one or more monovalent metal salts of an organic acid includes a sodium salt and/or potassium salt.

The one or more monovalent or divalent metal salts of an organic acid may be present in the salt-oxidation compositions of the present disclosure in an amount of from above 0 wt. % to about 70 wt. % or from about 0.01 wt. % to about 60 wt. % or from about 0.05 wt. % to about 50 wt. % or from about 0.1 wt. % to about 48 wt. % or from about 0.1 wt. % to about 40 wt. % or from about 0.15 wt. % to about 30 wt. % or from about 0.2 wt. % to about 20 wt. %, including all ranges and sub-ranges therebetween, based on the total weight of the salt-oxidation compositions.

In various embodiments, the one or more monovalent or divalent metal salts of an organic acid is present in the salt-oxidation compositions of the present disclosure in a wt. % amount of about 1, 5, 10, 15, 20, 25, 30, 31, 32, 33, 34, 35, 36, 37, 38, 39, 40, 41, 42, 43, 44, 45, 46, 47, 48, 49, 50, 55, 60, 65, or 70, based on the total weight of the salt-oxidation compositions.

In some embodiments, the one or more monovalent or divalent metal salts of an organic acid may be present in the hair coloring agents and/or the ready-to-use dye mixtures of the present disclosure in an amount of from above 0 wt. % to about 50 wt. % or from about 0.05 wt. % to about 30 wt. % or from about 0.1 wt. % to about 20 wt. % or from about 0.2 wt. % to about 20 wt. % or from about 0.2 wt. % to about 15 wt. % or from about 0.2 wt. % to about 10 wt. % or from about 0.2 wt. % to about 8 wt. %, or from about 0.3 wt. % to about 5 wt. %, or from about 0.5 wt. % to about 3 wt. %, including all ranges and sub-ranges therebetween, based on the total weight of the hair coloring agent and/or the ready-to-use dye mixtures.

In various embodiments, the one or more monovalent or divalent metal salts of an organic acid is present in the hair coloring agents and/or the ready-to-use dye mixtures of the present disclosure in a wt. % amount of about 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, or 6.5, based on the total weight of the hair coloring agent and/or the ready-to-use dye mixtures.

Antioxidants

Many antioxidants are useful in hair coloring compositions. For example, non-limiting examples of antioxidants include ascorbic acid, sodium sulfite, sodium metabisulfite, sodium hydrosulfite, tocopherols, alpha-tocopherol, tocopheryl acetate, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, and a mixture thereof. The selection of appropriate antioxidant(s) useful in a particular antioxidant booster composition may depend on a variety of factors, for example, the type of oxidative dye precursors of the hair coloring base composition, the types of optional couplers that may be present in the hair coloring base composition, etc. In some instances, the antioxidant booster composition includes ascorbic acid, sodium sulfite, sodium metabisulfite, or a mixture thereof.

The antioxidants may include flavonoids. Flavonoids exhibit chelating properties with metal ions and may reduce the oxidative damage from metal ions by sequestering the ions. Formation and stability of flavonoids-metal-chelates is a structure-dependent function. Flavonoids with a catechol moiety and with hydrogen bonds between hydroxyl group in the 5- and 3-positions have chelating properties.

Vitamin C and derivatives may be used, including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (*Myrciaria dubia*), acerola, *emblica officinalis*, and bioflavonoids from rose hip and citrus may be used including watersoluble bioflavonoids such as hesperidin methyl chalcone may also be used.

Other antioxidants, which may be incorporated, include tocopherols (e.g. d-α-tocopherol, d-β-tocopherol, d-γ-tocopherol, d-delta-tocopherol), tocotrienols (e.g. d-α-tocotrienol, d-β-tocotrienol, d-γ.-tocotrienol, d-delta-tocotrienol,) and vitamin E (α-tocopherol acetate). These compounds may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewer's grain or oats.

In addition, carotenoids, particularly the xanthophyll type, are also useful antioxidants that can be used. The xanthophyll type carotenoids include molecules, such as lutein, canthaxantin, cryptoxanthin, zeaxanthin and astaxanthin. Xanthophylls protect compounds, such as vitamin A, vitamin E and other carotenoids.

The flavonoid may be a flavanone (derivative of 2,3-dihydro-2-phenylchromen-4-one). Flavones include: Butin, Eriodictyol, Hesperetin, Hesperidin, Homoeriodictyol, Isosakuranetin, Naringenin, Naringin, Pinocembrin, Poncirin, Sakuranetin, Sakuranin, and Sterubin. The flavonoid may be a flavanonol (derivative of 3-hydroxy-2,3-dihydro-2-phenylchromen-4-one). Flavanols include: Taxifolin, Aromadedrin, Chrysandroside A, Chrysandroside B, Xeractinol, Astilbin, and Fustin. The flavonoid may be a flavone (derivative of 2-phenylchromen-4-one). Flavones include: Apigenin, Luteolin, Tangeritin, Chrysin, Baicalein, Scutellarein, Wogonin, Synthetic Flavones: Diosmin, and Flavoxate. The flavonoid may be a flavonol (derivative of 3-hydroxy-2-phenylchromen-4-one). Flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Hyperoside, Isoquercitin, Kaempferitrin, Myricitrin, Quercitrin, Robinin, Rutin, Spiraeoside, Xanthorhamnin, Amurensin, Icariin, and Troxerutin.

The antioxidant may be an anthocyanidin (derivative of 2-phenylchromenylium cation). Anthocyanidins include: Aurantinidin, Cyanidin, Delphinidin, Europinidin, Luteolinidin, Pelargonidin, Malvidin, Peonidin, Petunidin, Rosinidin, and Xanthone.

The antioxidant may be a dihydrochalcone (derivative of 1,3-diphenyl-1-propanone). Dihydrochalcones include: Phloretin, Dihydrochalcone phloretin Phlorizin, Aspalathin, Naringin dihydrochalcone, Neohesperidin dihydrochalcone, and Nothofagin. Without limiting the mode of action of the invention, dihydrochalcones may exert an antioxidant effect by reducing reactive free radicals, like reactive oxygen and reactive nitrogen species.

The antioxidant may be a Phenylpropanoid (derivatives of cinnamic acid). Phenylpropanoids include: Cinnamic acid, Caffeic acid, Ferulic acid, Trans-ferulic acid (including its antioxidant pharmacore 2,6-dihydroxyacetophenome), 5-Hydroxyferulic acid, Sinapic acid, Coumaryl alcohol, Coniferyl alcohol, Sinapyl alcohol, Eugenol, Chavicol, Safrole, P-coumaric acid, and Sinapinic acid. Without limiting the mode of action of the invention, Phenylpropanoids may neutralize free radicals. The antioxidant may be a Chalcone (derivative of 1,3-diphenyl-2-propen-1-one). Chalcones include: Butein, Okanin, Carthamin, Marein, Sophoradin, Xanthohumol, Flavokvain A, Flavokavain B, Flavokavin C., and synthetic Safalcone.

The one or more antioxidants may be present in the salt-oxidation compositions of the present disclosure in an amount of from above 0 wt. % to about 70 wt. % or from about 0.01 wt. % to about 60 wt. % or from about 0.05 wt. % to about 50 wt. % or from about 0.1 wt. % to about 48 wt. % or from about 0.1 wt. % to about 40 wt. % or from about 0.15 wt. % to about 30 wt. % or from about 0.2 wt. % to about 20 wt. %, including all ranges and sub-ranges therebetween, based on the total weight of the salt-oxidation compositions.

In various embodiments, the one or more antioxidants is present in the salt-oxidation compositions of the present disclosure in a wt. % amount of about 1, 5, 10, 15, 20, 25, 30, 31, 32, 33, 34, 35, 36, 37, 38, 39, 40, 41, 42, 43, 44, 45, 46, 47, 48, 49, 50, 55, 60, 65, or 70, based on the total weight of the salt-oxidation compositions.

In some embodiments, the one or more antioxidants may be present in the hair coloring agents and/or the ready-to-use dye mixtures of the present disclosure in an amount of from about 0.05 wt. % to about 10 wt. % or from about 0.1 wt. % to about 5 wt. %, or from about 0.2 wt. % to about 4 wt. %, or from about 0.3 wt. % to about 3 wt %, including all ranges and sub-ranges therebetween, based on the total weight of the hair coloring agents and/or the ready-to-use dye mixtures.

In various embodiments, the one or more antioxidants is present in the hair coloring agents and/or the ready-to-use dye mixtures of the present disclosure in a wt. % amount of about 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, or 6.5, based on the total weight of the hair coloring agent and/or the ready-to-use dye mixtures.

Colorants

The coloring compositions of the present disclosure include at least one colorant compound chosen from oxidative dye precursors, direct dyes, pigments, and mixtures thereof. The oxidation dyes are generally chosen from one or more oxidation bases optionally combined with one or more couplers. By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(.beta.-hydroxyethyl)-para-phenylenediamine, 4-N,N-bis(.beta.-hydroxyethyl)amino-2-methylaniline, 4-N,N-bis(.beta.-hydroxyethyl)amino-2-chloroaniline, 2-.beta.-hydroxyethyl-para-phenylenediamine, 2-methoxymethyl-para-phenylenediamine, 2-fluoro-para-phenylenediamine, 2-isopropyl-para-phenylenediamine, N-(.beta.-hydroxypropyl)-para-phenylenediamine, 2-hydroxymethyl-para-phenylenediamine, N,N-dimethyl-3-methyl-para-phenylenediamine, N-ethyl-N-(.beta.-hydroxyethyl)-para-phenylenediamine, N-(.beta.,.gamma.-dihydroxypropyl)-para-phenylenediamine, N-(4'-aminophenyl)-para-phenylenediamine, N-phenyl-para-phenylenediamine, 2-.beta.-hydroxyethyloxy-para-phenylenediamine, 2-.beta.-acetylaminoethyloxy-para-phenylenediamine, N-(.beta.-methoxyethyl)-para-phenylenediamine, 4-aminophenylpyrrolidine, 2-thienyl-para-phenylenediamine, 2-.beta.-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-.beta.-hydroxyethyl-para-phenylenediamine, 2-.beta.-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(.beta.-hydroxyethyl)-para-phenylenediamine, 2-chloro-para-phenylenediamine and 2-.beta.-acetylaminoethyloxy-para-phenylenediamine, and the addition salts thereof with an acid, are particularly preferred.

Among the bis(phenyl)alkylenediamines that may be mentioned, for example, are N,N'-bis(.beta.-hydroxyethyl)-N,N'-bis(4'-aminophenyl)-1,3-diaminopropano-I, N,N'-bis(.beta.-hydroxyethyl)-N,N'-bis(4'-aminophenyl)ethylenediamine, N,N'-bis(4-aminophenyl)tetramethylenediamine, N,N'-bis(.beta.-hydroxyethyl)-N,N'-bis(4-aminophenyl)tetramethylenediamin-e, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(.beta.-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds such as 2,5-diaminopyridine, 2-(4-methoxyphenyl)amino-3-aminopyridine and 3,4-diaminopyridine, and the addition salts thereof. Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-.quadrature.-hydroxyethoxy-3-amino-pyrazolo[1,5-a]pyridine; 2-(4-dimethylpyperazinium-1-yl)-3-amino-pyrazolo[1,5-a]pyridine; hydroxyethoxy aminpyrazolopyridine hydrochloride, 1-hydroxyethyl 4, 5-diamino pyrazole sulfate, and the addition salts thereof.

More particularly oxidation bases that are useful in the present disclosure are selected from 3-aminopyrazolo-[1,5-a]-pyridines and preferably substituted on carbon atom 2 by:

(a) one (di)($C_1$-$C_6$)(alkyl)amino group wherein said alkyl group can be substituted by at least one hydroxy, amino, imidazolium group;

(b) one heterocycloalkyl group containing from 5 to 7 members chain, and from 1 to 3 heteroatoms, potentially cationic, potentially substituted by one or more ($C_1$-$C_6$-alkyl, such as di(C1-C4)alkylpiperazinium; or (c) one ($C_1$-$C_6$)alkoxy potentially substituted by one or more hydroxy groups such as .quadrature.-hydroxyalkoxy, and the addition salts thereof.

Among the pyrimidine derivatives that may be mentioned are compounds such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are compounds such as 4,5-diamino-1-methyl-pyrazole, 4,5-diamino-1-(.beta.-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(.beta.-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(.beta.-hydroxyethyl)amino-1-methylpyrazole, and the addition salts thereof. 4,5-Diamino-1-(.beta.-methoxyethyl)pyrazole may also be used.

Pyrazole derivatives that may also be mentioned include diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-on-e, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol--3-one, 2,3-diamino-6-hydroxy-6,7-dihydro-1H,5H-pyrazolo[1,2-a]pyrazol-1-o-ne. 2,3-Diamino-6,7-dihydro-1H,5H-pyrazolo[1,2-a]pyrazol-1-one and/or a salt thereof will preferably be used. 4,5-Diamino-1-(.beta.-hydroxyethyl)pyrazole and/or 2,3-diamino-6,7-dihydro-1H,5H-pyrazolo[1,2-a]pyrazol-1-one and/or a salt thereof and/or 2,3-diaminodihydropyrazolo pyrazolone dimethosulfonate and/or a salt thereof, will preferentially be used as heterocyclic bases.

Composition according to the present disclosure may optionally comprise one or more couplers advantageously chosen from those conventionally used in the dyeing or coloring of keratin fibers.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(.beta.-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(.beta.-hydroxyethyloxy)benzene, 2-amino-4-(.beta.-hydroxyethylamino)-1-methoxybenzene, 1,3-diaminobenzene, 1,3-bis(2,4-diamino-phenoxy)propane, 3-ureidoaniline, 3-ureido-1-dimethylamino-benzene, sesamol, 1-.beta.-hydroxyethylamino-3,4-methylene-dioxybenzene, .alpha.-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(.beta.-hydroxyethyl)amino-3,4-methylene-dioxybenzene, 2,6-bis(J-hydroxyethylamino) toluene, 6-hydroxy-indoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the disclosure are especially selected from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of the compositions of the present disclosure.

The coupler(s), if they are present, each advantageously represent from 0.001% to 10% by weight relative to the total weight of the composition, and preferably from 0.005% to 5% by weight relative to the total weight of the compositions of the present disclosure.

Compositions according to the disclosure may optionally comprise b) one or more synthetic or natural direct dyes, chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Many direct dyes are cationic direct dyes. Mention may be made of the hydrazono cationic dyes of formulas (Va) and (V'a), the azo cationic dyes (VIa) and (VI'a) and the diazo cationic dyes (VIIa) below:

| | |
|---|---|
| Het$^+$—C(R$^a$)=N—N(R$^b$)—Ar, An$^-$ | (Va) |
| Het$^+$—N(R$^a$)—N=C(R$^b$)—Ar, An$^-$ | (V'a) |
| Het$^+$—N=N—Ar, An$^-$ | (VIa) |

-continued

| | |
|---|---|
| Ar$^+$—N=N—Ar'', An$^-$ | (VI'a) and |
| Het$^+$—N=N—Ar'—N=N—Ar, An$^-$ | (VIIa) | in which formulas (Va), (V'a), (VIa), (VI'a) and (VIIa):

Het$^+$ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;

Ar$^+$ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$)alkoxy Ar'' is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;

$R^a$ and $R^b$, which may be identical or different, represent a hydrogen atom or a group ($C_1$-$C_8$)alkyl, which is optionally substituted, preferentially with a hydroxyl group;

or alternatively the substituent $R^a$ with a substituent of Het$^+$ and/or $R_b$ with a substituent of Ar and/or $R^a$ with $R_b$ form, together with the atoms that bear them, a (hetero)cycloalkyl;

particularly, $R^a$ and $R_b$ represent a hydrogen atom or a group ($C_1$-$C_4$)alkyl, which is optionally substituted with a hydroxyl group;

An$^-$ represents an anionic counter-ion such as mesylate or halide. In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

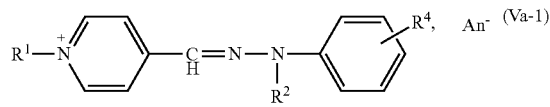

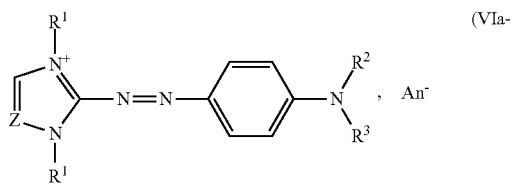

(VIa-1)

formulae (V-1) and (VI-1) with:

$R^1$ representing a $(C_1-C_4)$ alkyl group such as methyl;

$R^2$ and $R^3$, which are identical or different, represent a hydrogen atom or a $(C_1-C_4)$alkyl group, such as methyl; and $R^4$ represents a hydrogen atom or an electron-donating group such as optionally substituted $(C_1-C_8)$alkyl, optionally substituted $(C_1-C_8)$alkoxy, or $(di)(C_1-C_8)$(alkyl)amino optionally substituted on the alkyl group (s) with a hydroxyl group; particularly, $R^4$ is a hydrogen atom, Z represents a CH group or a nitrogen atom, preferentially CH;

An⁻ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

Basic Red 51

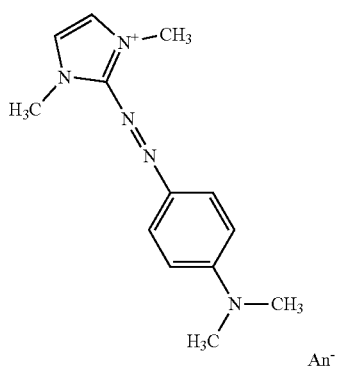

Basic Orange 31

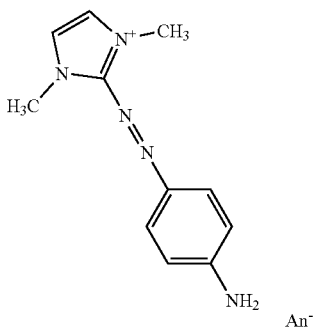

Basic Yellow 87

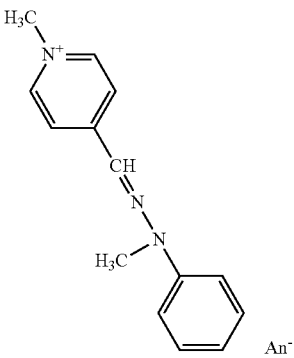

Among the natural direct dyes that may be used according to the disclosure, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the direct dye(s) more particularly represent from 0.001% to 10% by weight and preferably from 0.005% to 5% by weight of the total weight of the compositions of the present disclosure.

Alkalizing Agents

The hair coloring composition may have a pH that is alkaline. Exemplary pH's include 7, 8, 9, 10, 11, 12, 13 or 14. In some embodiments, the pH of the hair coloring composition may range from about 7, 8, or 9 to about 9, 10, 11 or 12.

The alkalinity of the hair coloring composition may be derived from one or more alkalizing agents. In some embodiments, the alkalizing agent may ammonia or an ammonia gas-generating compound and/or an amine or ammonium-based compound in amounts sufficient to make such compositions alkaline. In further embodiments, the alkalizing agent may be selected from alkanolamines, such as monoethanolamine (MEA) and isopropanolamine. Alkalinity may be derived from ammonium compounds as well (e.g., $NH_4OH$).

The one or more alkalizing agents may be present in amounts ranging from greater than about 0, or from 1, 2, 3, 4, 5, 10 to about 5, 10, 13, 15, 18, 20, 25 or 30% by weight of the total composition.

Oxidizing Agents

Oxidizing agents may be selected from, for example, peroxides, persulfates, perborates percarbonates, alkali metal bromates, ferricyanides, peroxygenated salts, or mixtures thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be employed as an oxidizing agent.

In some cases, the oxidizing agent is hydrogen peroxide present in an aqueous solution whose titre may range from 1 to 40 volumes, such as from 5 to 40 volumes or such as from 5 to 20 volumes.

In other cases, the oxidizing agent is a persulfate and/or a monopersulfate such as, for example, potassium persulfate, sodium persulfate, ammonium persulfate, as well as mixtures thereof. In one embodiment, the oxidizing agents in the present disclosure are selected from hydrogen peroxide, potassium persulfate, sodium persulfate, and mixtures thereof. Hydrogen peroxide may commonly be used as the oxidizing agent.

In an embodiment, the oxidizing agent is hydrogen peroxide and is provided as an oxidizing (developer) composition.

In general, the oxidizing agent will be present in an amount of from about 0.05 to about 50% by weight, such as from about 0.1% to about 30% by weight, or such as from about 0.1% to about 20% by weight, or such as from about 1% to about 10% by weight, based on the total weight of the oxidizing composition.

In some instances, the oxidizing composition is aqueous or is in the form of an emulsion.

In other instances, the oxidizing composition is substantially anhydrous. The term "substantially anhydrous" means that the oxidizing composition is either completely free of water or contains no appreciable amount of water, for example, no more than 5% by weight, or no more than 2% by weight, or no more than 1% by weight, based on the weight of the oxidizing composition. It should be noted that this refers for example to bound water, such as the water of crystallization of the salts or traces of water absorbed by the raw materials used in the preparation of the compositions according to the disclosure.

The oxidizing composition can contain at least one solvent, chosen from water, organic solvents, and mixtures thereof. When the oxidizing composition is substantially anhydrous, the oxidizing composition may comprise at least one solvent chosen from organic solvents. Suitable organic solvents for use in the oxidizing composition include ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

The organic solvent may, for example, be present in an amount ranging from about 0.5% to about 70% by weight, such as from about 2% to about 60% by weight, preferably from about 5 to about 50% by weight, relative to the total weight of the oxidizing composition.

The oxidizing composition may be in the form of a powder, gel, liquid, foam, lotion, cream, mousse, and emulsion.

The oxidizing composition of the present disclosure my also contain at least one fatty substance as described above. Thus, the total amount of fatty substances in the combination or mixture of the coloring and oxidizing compositions of the present disclosure may range from about 10% to about 80% by weight, or such as from about 20% to about 60% by weight, or such as from about 20% to about 40% by weight, or such as from about 20% to about 30% by weight, based on the total weight of the composition.

Cosmetically Acceptable Solvent (or Carrier)

The compositions of the present disclosure may be presented in a cosmetically acceptable solvent. This cosmetically acceptable solvent may include, for example, water or a mixture of water and at least one cosmetically acceptable organic solvent.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

Other suitable examples of organic solvents are ethylene glycol, propylene glycol, butylene glycol, hexylene glycol, propane diol, and glycerin.

The organic solvents for use in the present disclosure can be volatile or non-volatile compounds.

The cosmetically acceptable solvent may be employed according to the present disclosure in an amount ranging from about 5% to about 95% by weight, or such as from about 20% to about 90% by weight, such as from about 30 to about 80% by weight, or such as from about 35% to about 75% by weight, such as from about 5 to about 50% by weight, such as from about 50 to 95% by weight, based on the total weight of the composition.

The organic solvent may be employed according to the present disclosure in an amount ranging from about 0.1% to about 25% by weight, such as from about 1% to about 15% by weight, or such as from about 3% to about 10% by weight, or such as from about 5% to about 10% by weight, based on the total weight of the composition of the present disclosure.

Auxiliary Agents

Auxiliary ingredients may be added to the salt and antioxidant compositions, coloring agents, and/or oxidizing (developer) composition of the present disclosure. Exemplary auxiliary ingredients useful according to various embodiments of the disclosure include, but are not limited to, rheology-modifying agents or polymers, surfactants (cationic, anionic, non-ionic and/or amphoteric/zwitterionic surfactants), cationic polymers, bleach activators and co-bleach activators, chelants, fatty substances, ceramides, alkoxyaminosilicones, silanes, and lift-enhancing agents, such as nitrogen-containing compounds and metal catalyst compounds, and preservatives.

The coloring and/or oxidizing (developer) composition may also contain acid and alkali pH adjusters, which are well known in the art in the cosmetic treatment of keratin fibers, such as hair. Such pH adjusters include, but are not limited to, sodium metasilicate, silicate compounds, citric acid, ascorbic acid, and carbonate compounds.

The compositions and agents of the present disclosure may contain one or more rheology or viscosity modifying agents, such as viscosity increasing agents. Classes of such agents include, but are not limited to, viscous liquids, such as polyethylene glycol, semisynthetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof.

Forms

The compositions and coloring agents described herein may be in any suitable physical form. Suitable forms include, but are not limited to low to moderate viscosity liquids, creams, lotions, milks, mousses, sprays, gels, and the like. Suitable excipients, such as those listed above, are included or excluded from the hair coloring formulation depending on the form of use of the formulation (e.g., spray, cream, gel, etc.).

i. Creams

The compositions and coloring agents disclosed herein for coloring hair may be in the form of a cream. The cream can be prepared as emulsions, for example, oil in water or water in oil or water in oil in water emulsions and will generally contain one or more of emulsifying agents, nonionic surfactants, anionic surfactants, cationic agents, conditioning agents, fatty alcohols, oils, and mixtures thereof.

ii. Gels

The compositions and coloring agents disclosed herein for coloring hair may be in the form of a gel. The gels will typically contain a cosmetically acceptable carrier such as water and will generally contain one or more of gelling agents, structuring agents, rheology or viscosity modifying agents, and mixtures thereof.

iii. Spray

The compositions and coloring agents described herein for coloring hair may be in the form of a spray. The spray typically includes the coloring composition in a cosmetically acceptable carrier. In some embodiments, the carrier is water or a water and alcohol mixture. The spray formulation optionally includes an emollient, thickener, hair conditioning agent, polymer, and/or surfactant. The hair spray formulations may be dispensed from containers that include aerosol dispensers or pump spray dispensers. Such dispensers are known in the art and are commercially available from a variety of manufacturers.

When the hair spray formulation is dispensed from a pressurized aerosol container, a propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed.

The amount of propellant may range from about 10% to about 60% by weight of the formulation. The propellant may be separated from the hair color formulation as in a two compartment container. Other suitable aerosol dispensers are those characterized by the propellant being compressed air, which can be filled into the dispenser using a pump or equivalent device prior to use. Conventional non-aerosol pump spray dispensers, i.e., atomizers, may also be used to apply the hair strengthening formulation to the hair.

Compositions, Kits, and Methods

The invention of the present disclosure pertains to a hair coloring agent containing, in a cosmetically acceptable solvent:

(a) one or more divalent metal salts of an inorganic acid;
(b) one or more monovalent or divalent metal salts of an organic acid;
(c) one or more antioxidants; and
(d) one or more colorants chosen from oxidative dye precursors, direct dyes, pigments, and mixtures thereof.

The invention of the present disclosure also pertains to a hair coloring agent containing, in a cosmetically acceptable solvent:

(a) one or more divalent metal salts of an inorganic acid in an amount of from about 0.05 wt. % to about 20 wt. %;

wherein the metal salts are chosen from metal salts of halides, metal hydroxides, metal sulfates, metal oxides, and mixtures thereof; and wherein the divalent metal is calcium, zinc, iron, nickel, copper, silver, magnesium, strontium, barium, manganese, or cobalt; and (b) one or more monovalent or divalent metal salts of an organic acid in an amount of from about 0.1 wt. % to about 20 wt. %;

wherein the metal salts are chosen from salts of lithium, sodium, potassium, copper, silver, and mixtures thereof; and wherein the divalent metal is calcium, zinc, iron, nickel, copper, silver, magnesium, strontium, barium, manganese, or cobalt;

wherein the monovalent metal salt is lithium, sodium, potassium, copper, or silver;

wherein the organic acid is chosen from C1 to C9 monocarboxylic or di-carboxylic acids, polycarboxylic acids, hydroxy-carboxylic acids, fatty acids having at least 10 carbon atoms, including organic acids with heterocyclic groups, for example, ascorbic acid, formic acid, acetic acid, glycolic acid, gluconic acid, lactic acid, mandelic acid, oxalic acid, maleic acid, malonic acid, glyoxylic acid, succinic acid, adipic acid, fumaric acid, sebacic acid, including citric acid, tartaric acid, malic acid, 2-hydroxy malonic acid, 2-hydroxyl n-butyl 1,2,4-tricarboxylic acid, glutaric acid, glucaric acid, 2-hydroxy n-butyl 1,3,4-tricarboxylic acid, pyrrolidone carboxylic acid, phenolsulfonic acid, and salicylic acid;

(c) one or more antioxidants in an amount of from about 0.1 wt. % to about 10 wt. %; and wherein the antioxidants are chosen from ascorbic acid and its derivatives, sodium sulfite, sodium metabisulfite, sodium hydrosulfite, tocopherols, alpha-tocopherol, tocopheryl acetate, EDTA, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, Butylated hydroxytoluene (BHT), Butylated hydroxyanisole (BHA), N,N'-bis(3,4,5-trimethoxybenzyl)ethylenediamine and its salts, and mixtures thereof (d) one or more colorants chosen from oxidative dye precursors, direct dyes, pigments, and mixtures thereof;

all weight being based on the total weight of the hair coloring agent.

Any of the above hair coloring agents may further comprise a developer containing an oxidizing agent (e.g., hydrogen peroxide) and/or alkalizing agent in order to form a ready to use hair dye composition.

In an embodiment of the present disclosure, a monovalent or divalent metal salt of an organic acid (e.g. zinc-based compound) and/or a divalent metal salt of an organic acid (e.g. an alkaline earth metal salt such as a calcium chloride) and/or an antioxidant are first added as separate components or as one salt-antioxidant component into a hair colorant composition containing one or more colorants chosen from oxidative dye precursors, direct dyes, pigments, and mixtures thereof in order to form a hair coloring agent. The developer is then combined with the hair coloring agent.

In an embodiment of the present disclosure, a dye mixture is first formed from the combination of the colorant composition containing one or more colorants chosen from oxidative dye precursors, direct dyes, pigments, and mixtures thereof and the oxidizing or developer composition.

The monovalent or divalent metal salt of an organic acid (e.g. zinc-based compound) and/or a divalent metal salt of an inorganic acid (e.g. an alkaline earth metal salt such as a calcium chloride) and/or antioxidant are then added as separate components or as one salt-antioxidant component into the dye mixture to form a ready to use hair dye composition.

Another aspect of the invention pertains to kits comprising the coloring and developer compositions described herein. For example, developer may be present in a separate container from the coloring composition which comprises the above-described metal salts, antioxidants, and colorants. The coloring composition may, in some embodiments, be ready for mixing with the developer. In such embodiments, the developer and hair coloring agent are combined just prior to use.

In other embodiments, each of the above-described components of the hair coloring agent (metal salts, antioxidants, and colorants) are packaged in separate containers. In an embodiment, the one or more divalent metal salts of an inorganic acid (a), the one or more monovalent or divalent metal salts of an organic acid (b), the one or more antioxidants (c), and the one or more colorants chosen from oxidative dye precursors, direct dyes, pigments, and mixtures thereof (d) can be packaged in separate containers. In another embodiment, the metal salts (a) and (b) can be packaged together in one container, the antioxidants can be packaged in a second container, and the colorants can be packaged in a third container. In yet another embodiment, one of the metal salts (a) or (b) and the antioxidants (c) can be packaged with the colorants (d) in one container and the remaining metal salt component or antioxidant is packaged in separate containers. The contents of the containers in these various embodiments can then be mixed in any order to form the hair coloring agent.

In an embodiment, when the one or more metal salt components (a) or (b) or antioxidants (c) are packaged separately from the colorants, the metal salt component and/or antioxidant can first be mixed with the developer composition followed by addition of the colorants in order to form a ready to use dye composition.

When the one or more of the metal salt components (a) or (b) or antioxidant (c) are packaged separately from the colorants, the metal salt component and/or antioxidants can be in anhydrous or substantially anhydrous form (for example, powder or wet powder form) or in liquid form (for example, aqueous or emulsion/lotion or serum form in a cosmetically acceptable solvent such as water and/or organic solvents).

Another aspect of the invention pertains to methods of using the coloring compositions and dye compositions resulting from the combination of the metal salts, antioxidants, coloring composition and oxidizing composition (developer) of the present disclosure. The methods comprise applying the dyes compositions described herein to human hair. The dye composition may be left on the hair for a period of time sufficient to achieve the desired alteration in hair tone. For example, the dye composition may be left on the hair for up to one hour, such as from about 3 minutes to about 45 minutes, from about 5 minutes to about 30 minutes, or from about 10 minutes to about 20 minutes. In further embodiments, the dye composition may be left on the hair for a period up to about 30 minutes, such as, for example, from about 1 to about 30 minutes, about 1 to about 10 minutes, or about 1 to about 5 minutes. One skilled in the art will, by considering various factors such as the starting and desired tones of the hair, be able to determine an appropriate amount of time to leave the dye composition on the hair in order to achieve the desired alteration in hair tone. By way of non-limiting example, various embodiments according to the disclosure may provide for an increase of 1 to 4 in the tone height of the hair.

In some embodiments, the dye composition may, optionally, be shampooed and/or rinsed off the hair.

Thus, another aspect of the invention pertains to a method for artificially coloring hair and/or inhibiting the artificial coloring from fading, the method comprising contacting hair with the above-described ready to use dye compositions for a sufficient period of time to achieve a desired color of the hair and/or alteration of the color of hair.

Implementation of the present disclosure is provided by way of the following examples. The examples serve to illustrate the technology without being limiting in nature.

EXAMPLES

General Procedures

90% gray permed hair swatches (from International Hair Importers, HIP) were treated and evaluated as set forth below.

General Coloration Process: The hair swatches were colored/dyed with a dye mixture formed from combining a coloring composition and a developer composition for a period of time to give a desired color to the hair. The coloring composition contained oxidative dyes and the developer contained an oxidizing agent (hydrogen peroxide). The developer composition can employ different amounts of the oxidizing agent depending on the desired lift or lightening of the color on the hair. For example, a 20 volume developer means that it contains 6 wt. % of an oxidizing agent; a 10 volume developer means that it contains 3 wt. % of an oxidizing agent; a 3 volume developer means that it contains 0.9 wt. % of an oxidizing agent.

In an embodiment, the coloring composition is in the form of a cream or an emulsion cream.

The weight ratio of the coloring composition to the developer in the present disclosure can range from about 1:4 to about 5:0.2, or from about 1:3 to about 4.8:0.2, or from about 1:2 to about 4.8:0.2, or from about 1.5:2 to about 4.8:0.2, or from about 1.5:2.25 to about 4.8:0.2, or from about 1:2 to about 2:1, or from about 1:1 to about 4.8:0.2.

In various embodiments, the weight ratio of the coloring composition to the developer in the present disclosure is at about 2:3, or about 3:3, or about 1:2, or about 2:2, or about 1:1, or about 1.5:2, or about 1.5:2.25, or about 1:1.5, or about 1.5:1.5 (or 1), or about 1.5:2.5, or about 4:1, or about 3:0.5, or about 4.8:0.2.

In various embodiments and in accordance with the present disclosure, a composition containing a divalent metal salt of an inorganic acid (e.g., calcium chloride), a divalent metal salt of an organic acid (e.g., zinc gluconate), and an antoixidant, a colorant composition (or hair coloring composition) containing a colorant, and a developer composition containing an oxidizing agent are combined together in order to form a dye mixture for coloring hair.

For example, a hair coloring composition containing a colorant, a divalent metal salt of an inorganic acid (e.g., calcium chloride), a divalent metal salt of an organic acid (e.g., zinc gluconate), and an antioxidant can be combined with a developer composition containing an oxidizing agent in order to form a dye mixture for coloring hair.

In an example, within two hours of coloring or dyeing hair, a divalent metal salt of an inorganic acid (e.g., calcium chloride), a divalent metal salt of an organic acid (e.g., zinc gluconate), and an antioxidant can be combined with a colorant or hair coloring composition containing colorant, resulting in a composition that is to be mixed with a developer composition.

In an example, within two hours of coloring or dyeing hair, one or more of a divalent metal salt of an inorganic acid, or of a divalent metal salt of an organic acid, or of an antioxidant can be combined with a colorant or hair coloring composition containing colorant and one or more of a divalent metal salt of an inorganic acid, or of a divalent metal salt of an organic acid, or of an antioxidant, resulting in a composition that is to be mixed with a developer composition. Various combinations can be contemplated. For example, a divalent metal salt of an inorganic acid and a divalent metal salt of an organic acid can be combined with a hair coloring composition containing colorant and an antioxidant, resulting in a composition that is to be mixed with a developer composition. In another example, a divalent metal salt of an inorganic acid and an antioxidant are added to a hair coloring composition containing colorant and a divalent metal salt of an organic acid, resulting in a composition that is to be mixed with a developer composition. Or, for example, a divalent metal salt of an organic acid and an antioxidant can be combined with a hair coloring composition containing colorant and a divalent metal salt of an inorganic acid, resulting in a composition that is to be mixed with a developer composition. Or, for example, an antioxidant can be combined with a hair coloring composition containing colorant, a divalent metal salt of an inorganic acid, and a divalent metal salt of an organic acid, resulting in a composition that is to be mixed with a developer composition.

In other examples and in accordance with the present disclosure, one or more of a divalent metal salt of an inorganic acid (e.g., calcium chloride), a divalent metal salt of an organic acid (e.g., zinc gluconate), and an organic acid, can be combined with a dye mixture formed from the combination of a colorant or hair coloring composition with a developer.

Hair Color Protection Evaluation:

The treated (dyed) hair swatches were washed with a shampoo (sodium laureth sulfate shampoo), then rinsed with water (a shampoo cycle). The hair swatches were then blow dried. For evaluations of hair color protection or wash-resistant hair color, the color of the dyed hair was assessed after one or more shampoo cycles (can range from one up to twenty shampoo cycles).

Hair Color Deposit Evaluation:

The treated hair swatches were rinsed with water and dried. The color of the dyed hair was then assessed.

Color Assessment:

For determining the degree of change in the color of hair and/or the degree of lightening of the color or degree of color deposit on hair, colorimetric measurements of L*, a*, and b* values of the hair swatches were obtained. The L*a*b* colorimetric system is a colorimetric system that assigns each color to a position in a spherical color space. In this color space, the brightness is represented by a position in the ordinate (z-axis) direction, the hue is represented by a position in the circumferential direction, and the chroma is represented by a distance from the center axis. The position on the ordinate (z-axis) representing brightness is designated by L*, and the L* value changes from 0 corresponding to black to 100 corresponding to white. The positive direction of the x-axis corresponds to a red direction, the positive direction of the y-axis corresponds to a yellow direction, the negative direction of the x-axis corresponds to a green direction, the negative direction of the y-axis corresponds to a blue direction, and the position on the x-axis is designated by a* of which value changes from −60 to +60 and the position on the y-axis is designated by b* of which value changes from −60 to +60. The hue and chroma are represented by a* value and b* value, respectively.

Thus, the greater the value of L*, the lighter or less intense is the color of the hair. Conversely, the lower the value of L*, the darker or more intense is the color of the hair (this can also indicate greater color deposit when the hair is colored or dyed). The a* value (green/red color axis) and b* value (blue/yellow color axis) represent hue and chroma, respectively. The higher the a*, the more the hue shifts to red (i.e., the hair is redder); and the lower the b*, the more the chroma value shifts to blue. Delta-E (LE or dE) which is calculated from the L*, a*, and b* values represents the overall color change on the swatches (from control or baseline). Generally, if ΔE is less than 1.0 there is hardly any color difference that the human eye can see. If ΔE is greater than 1.0, then there is a noticeable color difference.

For control treatments in assessing the performance of the invention, the control coloring composition does not contain one or more of the divalent metal salt of an organic acid, the divalent metal salt of an inorganic acid, and the organic acid; instead, water in an amount equivalent to that of the total amount of metal salts and/or organic acid used was added to the colorant composition.

For control treatments in assessing the performance of the invention, the dye mixture does not contain one or more of a divalent metal salt of an inorganic acid (e.g., calcium chloride), a divalent metal salt of an organic acid (e.g., zinc gluconate), and an organic acid; instead, water in an amount equivalent to that of the total amount of metal salts and/or organic acid used was added to the dye mixture.

Example 1 Color Deposit and Color Protection

In this example, the hair swatches were dyed according to the weight ratio of 1 g hair:1.5 g of colorant composition:1.5 g of 20 vol peroxide developer (hydrogen peroxide), i.e., for every gram of hair, a total amount of three grams of a dye mixture (colorant composition plus developer composition) was used to dye the hair.

The dye mixture (ready-to-use composition for coloring hair) according to the invention was prepared by combining a 0.376 g of a powder composition containing 44.4 wt. % of zinc gluconate, 11.2 wt. % of calcium chloride, and 44.4 wt. % of ascorbic acid, 8.37 g of a colorant composition containing oxidative dye precursors and a cosmetically acceptable solvent, and 8.37 g of a developer composition containing oxidizing agents and a cosmetically acceptable solvent.

The dye mixture was allowed to remain on hair for 30 min after which the hair was rinsed and dried to remove excess dye. The hair dye mixture imparted a red color to hair.

Example 1A (Color Deposit)

Colorimetric measurements were taken to assess the degree of color deposit onto the swatches after the initial coloration. Color deposit was reported as L* values.

TABLE 1

Dye mixture composition; % values of the
actives (salts and antioxidant) are based on the
weight of the active relative to [developer + colorant] weight

| Formulas | Zinc Gluconate % | Calcium Chloride % | Ascorbic acid % | L @ 0x shampoo |
|---|---|---|---|---|
| Standard | — | — | — | 24.17 |
| SALTS control | 0.98% | 0.20% | — | 22.21 |
| Antioxidant Control | — | — | 0.98% | 21.66 |
| Inventive FLA | 0.98% | 0.20% | 0.98% | 20.64 |

Summary: The colorimetric L value for the inventive formula was the lowest value, demonstrating that the color of the hair was darker, thereby indicating more color deposit. The color of the hair dyed with the inventive formula was visually distinguishable (through a deeper, richer color) from the color of the hair dyed with the control and standard dye mixtures.

Example 1B ((Hair Color Protection)

L*a*b Colorimetry was used to measure the color evolution of the swatches over the 10 shampoo cycles. Measurements were taken after the initial coloration and after the 10th and final shampoo cycle. The change in the total color (dE) was then calculated based on the change between these values.

TABLE 2

Dye mixture composition; % values
of the actives (salts and antioxidant) are based on the
weight of the active relative to [developer + colorant] weight

| Formulas | Zinc Gluconate % | Calcium Chloride % | Ascorbic acid % | dE @ 10x Shampoo |
|---|---|---|---|---|
| Standard | — | — | — | 7.5 |
| SALTS control | 0.98% | 0.20% | — | 5.8 |
| Antioxidant Control | — | — | 0.98% | 5.1 |
| Inventive FLA | 0.98% | 0.20% | 0.98% | 3.9 |

Summary: The inventive formula demonstrated the lowest dE value after 10 shampoo cycles indicating the least amount of color fading. The color of the hair dyed with the inventive formula was visually distinguishable (through a deeper, richer color) from the color of the hair dyed with the control and standard dye mixtures.

Thus, surprisingly and unexpectedly, after the initial coloration process, the hair treated according to the invention exhibited a darker color which indicates better color deposit. It was also surprisingly and unexpectedly discovered that after 10 shampoos, the change in the color of the swatches treated with the dye mixture containing calcium chloride, zinc gluconate, and ascorbic acid was significantly less as compared to the change in the color of the swatches treated with the control and standard dyes. This shows that the color on the hair treated according to the invention was resistant to fading or shampoo-resistant even after 10 shampoo/wash cycles.

The colorimetric results also correspond to the visual observations wherein the differences in color deposition and delta-E can be perceived by the eye.

From the results above, it is evident that the hair treated according to the inventive method and compositions exhibited significant improvements in the amount of color deposited onto the hair and degree of color change when subjected to shampooing. The durability of the color in the hair that was treated according to the inventive method and compositions over multiple washings/shampooings (up to as much as 10 shampoos) is evident.

Example 2 Colorant-Developer+Salt-Antioxidant Mixtures (Ready-to-Use Dye Mixture Varying final amounts of the salts and antioxidant were tested in the colorant-developer mixture in order to obtain desirable results for the following parameters: mix aspect, mix viscosity and mix temperature using several commercial hair dyeing products (colorants, developers and optionally, ampoules containing cosmetic additives. Mix aspect is an indication of how easy it is to mix the compositions together (mixing efficiency). It was observed that the mixing efficiency and amount of antioxidant can depend on the containers or packaging in which the colorant and developer are combined. The mix viscosity of various commercial colorant-developer+salt-antioxidant mixture (ready-to-use dye mixture) ranged from ≥40 UD (spindle #2, 60s) to about 40 UD (spindle #3, 30s) or was greater or equal to 13 UD (spindle #3, 30s). UD is Units of deflection as measured by the Rheomat instrument. A spindle with a higher number is used for more viscous compositions.

The amount of the antioxidant in the final colorant-developer mixture was such that the mix temperature was not higher than body temperature or about 37° C. Thus, the final amount of the antioxidant (ascorbic acid) based on the total weight of the colorant-developer mixture resulted in a mix temperature of not greater than about 37° C. This final amount was also found to be dependent on the mixing container or device employed. For example, final amounts of antioxidant of from about 0.4 to about 0.6 wt. % were used when the colorant and developer are mixed in a bottle and higher amounts of antioxidant can be used when the colorant and developer are mixed in a bowl and the mixture is applied onto hair with an applicator.

In some examples, the colorant and developer kit or system include at one or more ampoules that contain cosmetic additives such as fragrance and/or other cosmetic ingredients. Thus, the starting weight of the colorant-developer mixture or colorant-developer-ampoule mixture before adding the anti-oxidant ranged from about 117 g to about 147 g.

TABLE 3

Salt-Antioxidant Combination

| Ingredient INCI US NAME | WT. % |
|---|---|
| CALCIUM CHLORIDE | 11.67 |
| ZINC GLUCONATE | 46.66 |
| ASCORBIC ACID | 41.67 |

Example 2A

The ready-to use dye mixture was formed according to the following:

The combination of 45 g colorant+67.5 g developer+4.5 ml ampoule (with cosmetic additives) (total amount of 117 g) was combined with 2.2 g of the Salt-Antioxidant combination in Table 3. The final amounts of the salts and antioxidant in the ready-to use dye mixture are:

1.03 g zinc gluconate/119.2 g=0.864% wt/wt
0.26 g calcium chloride/119.2 g=0.218% wt/wt
0.92 g ascorbic acid/119.2 g=0.772% wt/wt Example 2B The ready-to use dye mixture was formed according to the following:
The combination of 56 g colorant+84 developer+4.7 ml ampoule (with cosmetic additives) (total amount of 144.7 g) was combined with 2.2 g of the Salt-Antioxidant combination. The final amounts of the salts and antioxidant in the ready-to use dye mixture are:
1.03 g zinc gluconate/146.9 g=0.701% wt/wt
0.26 g calcium chloride/146.9 g=0.177% wt/wt
0.92 g ascorbic acid/146.9=0.626% wt/wt Example 2C: Lower Amounts of Antioxidant Ex. 2C1

1.6 g of zinc gluconate+calcium chloride/119.2 g colorant-developer mixture=1.34% wt/wt
0.6 g of ascorbic acid/119.2 colorant-developer mixture=0.503% wt/wt Ex. 2C2

1.6 g of zinc gluconate+calcium chloride/146.9 g colorant-developer mixture=1.1% wt/wt
0.6 g of ascorbic acid/146.9 colorant-developer mixture=0.408% wt/wt All values set forth herein can be modified with the term "about," if desired to impart the meaning above, or recited without the term in order to have their ordinary meaning, regardless of whether the term "about" is specifically set forth (or is absent) in conjunction with any particular value in the specification.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair coloring agent comprising one or more compositions containing:
  (a) one or more divalent metal salts of an inorganic acid chosen from salts of calcium, zinc, iron, nickel, copper, silver, magnesium, strontium, barium, manganese, cobalt, and mixtures thereof;
  (b) one or more monovalent or divalent metal salts of an organic acid, wherein
    the one or more divalent metal salts of an organic acid are chosen from salts of calcium, zinc, iron, nickel, copper, silver, magnesium, strontium, barium, manganese, cobalt, and mixtures thereof,
    the one or more monovalent metal salts of an organic acid are chosen from salts of lithium, sodium, potassium, copper, silver, and mixtures thereof, and
    the organic acid of the one or more monovalent or divalent metal salts of an organic acid is chosen from C1 to C9 monocarboxylic or di-carboxylic acids, polycarboxylic acids, hydroxy-carboxylic acids, fatty acids having at least 10 carbon atoms, and organic acids with heterocyclic groups;
  (c) one or more antioxidants; and
  (d) one or more colorants chosen from oxidative dye precursors, direct dyes, pigments, and mixtures thereof;
    wherein the weight ratio of the one or more divalent metal salts of an inorganic acid to the one or more monovalent or divalent metal salts of an organic acid and to the one or more antioxidants is at about (0.05-1):(0.1-5):(0.1-5).

2. The hair coloring agent of claim 1, wherein the one or more divalent metal salts of an inorganic acid are chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

3. The hair coloring agent of claim 1, wherein the one or more divalent metal salts of an inorganic acid includes a calcium salt.

4. The hair coloring agent of claim 3, wherein the calcium salt is calcium chloride.

5. The hair coloring agent of claim 1, wherein the one or more divalent metal salts of an organic acid are chosen from zinc lactate, zinc gluconate, zinc phenolsulfonate, zinc salicylate, zinc pyrrolidone carboxylic acid (Zinc PCA), zinc citrate, zinc ascorbate, their salt derivatives thereof, and mixtures thereof.

6. The hair coloring agent of claim 1, wherein the one or more divalent metal salts of an organic acid includes a zinc salt.

7. The hair coloring agent of claim 6, wherein the zinc salt is zinc gluconate.

8. The hair coloring agent of claim 1, wherein the one or more monovalent metal salts of an organic acid are chosen from sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof.

9. The hair coloring agent of claim 1, wherein the one or more antioxidants are chosen from ascorbic acid and its derivatives, sodium sulfite, sodium metabisulfite, sodium hydrosulfite, tocopherols, alpha-tocopherol, tocopheryl acetate, EDTA, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, Butylated hydroxytoluene (BHT), Butylated hydroxyanisole (BHA), N,N'-bis(3,4,5-trimethoxybenzyl)ethylenediamine and its salts, and mixtures thereof.

10. The hair coloring agent of claim 1 comprising:
  i. a composition comprising the (a) one or more divalent metal salts of an inorganic acid; the (b) one or more monovalent or divalent metal salts of an organic acid; and the (c) one or more antioxidants; and ii. a colorant composition comprising the (d) one or more colorants.

11. The hair coloring agent of claim 10, wherein the composition comprises:
at least 5 wt. % of the one or more divalent metal salts of an inorganic acid;
at least 10 wt. % of the one or more monovalent or divalent metal salts of an organic acid; and
at least 10 wt. % of the one or more antioxidants;
all weights being based on the total weight of the salt-antioxidant composition.

12. The hair coloring agent of claim 1, wherein the one or more divalent metal salts of an inorganic acid, the one or more monovalent or divalent metal salts of an organic acid, the one or more antioxidants, and the one or more colorants are contained in a single coloring composition.

13. The hair coloring agent of claim 1, further comprising an oxidizing composition comprising one or more oxidizing agents chosen from peroxides, persulfates, perborates, percarbonates, alkali metal bromates, ferricyanides, laccases, peroxidases, redox enzymes, their salts thereof, and mixtures thereof.

14. The hair coloring agent of claim 13, wherein the hair coloring agent comprises:
from about 0.01 wt. % to about 5 wt. % of the one or more divalent metal salts of an inorganic acid;
from about 0.25 wt. % to about 10 wt. % of the one or more monovalent or divalent metal salts of an organic acid; and
from about 0.05 wt. % to about 10 wt. % of the one or more antioxidants; and
a cosmetically acceptable solvent;
all weights being based on the total weight of the hair coloring agent.

15. The hair coloring agent of claim 14, wherein the weight ratio of the one or more divalent metal salts of an inorganic acid to the one or more monovalent or divalent metal salts of an organic acid and to the one or more antioxidants is at about (0.05-1):(0.1-5):(0.1-5).

16. A hair coloring agent comprising:
(a) a salt-antioxidant composition comprising:
i. one or more divalent metal salts of an inorganic acid present in an amount of at least 5 wt. %, based on the total weight of the salt-antioxidant composition, and chosen from metal halides, metal hydroxides, metal sulfates, metal oxides, and mixtures thereof; and wherein the divalent metal is calcium, zinc, iron, nickel, copper, silver, magnesium, strontium, barium, manganese, or cobalt;
ii. one or more monovalent or divalent metal salts of an organic acid present in an amount of at least 10 wt. %, based on the total weight of the salt-antioxidant composition, and chosen from metal ascorbates, formates, acetates, glycolates, gluconates, lactates, mandelates, oxalates, maleates, malonates, glyoxylates, succinates, adipates, fumarates, sebacates, citrates, tartarates, malates, tricarboxylates, glutarates, glucarates, pyrrolidone carboxylates, phenolsulfonate, salicylates, their salt derivatives thereof, salts of fatty acids having at least 10 carbon atoms, and mixtures thereof; wherein the monovalent metal is lithium, sodium, potassium, copper, or silver; and wherein the divalent metal is calcium, zinc, iron, nickel, copper, silver, magnesium, strontium, barium, manganese, or cobalt;
iii. one or more antioxidants are present in an amount of at least 10 wt. %, based on the total weight of the salt-antioxidant composition, and chosen from ascorbic acid and its derivatives, sodium sulfite, sodium metabisulfite, sodium hydrosulfite, tocopherols, alpha-tocopherol, tocopheryl acetate, EDTA, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, Butylated hydroxytoluene (BHT), Butylated hydroxyanisole (BHA), N,N'-bis(3,4,5-trimethoxybenzyl)ethylenediamine and its salts, and mixtures thereof;
(b) a colorant composition comprising one or more colorants chosen from oxidative dye precursors, direct dyes, pigments, and mixtures thereof; and a cosmetically acceptable solvent; and
(c) an oxidizing composition comprising:
(i) one or more oxidizing agents chosen from peroxides, urea peroxide, alkali metal bromates, ferricyanides, peroxygenated salts, perborates, percarbonates, laccases, peroxidases, redox enzymes, and mixtures thereof; and
(ii) a cosmetically acceptable solvent chosen from water and a water/organic solvent mixture;
wherein the salt-antioxidant composition, the colorant composition and the oxidizing composition are combinable to form a ready-to-use dye composition for artificially coloring hair.

17. The hair coloring agent of claim 16, wherein the one or more divalent metal salts of an inorganic acid are chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

18. The hair coloring agent of claim 16, wherein the one or more monovalent or divalent metal salts of an organic acid are chosen from zinc lactate, zinc gluconate, zinc phenolsulfonate, zinc salicylate, zinc pyrrolidone carboxylic acid (Zinc PCA), zinc citrate, zinc ascorbate, sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, their salt derivatives thereof, and mixtures thereof.

19. The hair coloring agent of claim 16, wherein the one or more organic acids are chosen from ascorbic acid and ascorbic acid derivatives.

20. The hair coloring agent of claim 16, wherein when the salt-oxidant composition, the colorant composition, and the oxidizing composition are combined, the one or more divalent metal salts of an inorganic acid is present in an amount of from about 0.05 wt. % to about 10 wt. %, the one or more monovalent or divalent metal salts of an organic acid is present in an amount of from about 0.2 wt. % to about 20 wt. %, and the one or more antioxidants is present in an amount of from about 0.2 wt. % to about 3 wt. %, all weights being based on the total weight of the hair coloring agent.

21. A method for artificially coloring hair and/or inhibiting the artificial coloring from fading, the method comprising:
- (1) combining the hair coloring agent of claim 1 with an oxidizing composition in order to form a ready-to-use dye composition, wherein the oxidizing composition contains:
  - (i) one or more oxidizing agents chosen from peroxides, urea peroxide, alkali metal bromates, ferricyanides, peroxygenated salts, perborates, percarbonates, laccases, peroxidases, redox enzymes, and mixtures thereof, and
  - (ii) a cosmetically acceptable solvent selected from water and a water/organic solvent mixture; and
- (2) contacting hair with the ready-to-use dye composition for a sufficient period of time to achieve a desired color of the hair and/or alteration of the color of hair.

22. A multi-compartment kit for altering the color of hair, the kit comprising:
- (1) a first unit containing:
  - (a) one or more divalent metal salts of an inorganic acid chosen from salts of calcium, zinc, iron, nickel, copper, silver, magnesium, strontium, barium, manganese, cobalt, and mixtures thereof;
  - (b) one or more monovalent or divalent metal salts of an organic acid, wherein
    - the one or more divalent metal salts of an organic acid are chosen from salts of calcium, zinc, iron, nickel, copper, silver, magnesium, strontium, barium, manganese, cobalt, and mixtures thereof,
    - the one or more monovalent metal salts of an organic acid are chosen from salts of lithium, sodium, potassium, copper, silver, and mixtures thereof, and
    - the organic acid of the one or more monovalent or divalent metal salts of an organic acid is chosen from C1 to C9 monocarboxylic or di-carboxylic acids, polycarboxylic acids, hydroxy-carboxylic acids, fatty acids having at least 10 carbon atoms, and organic acids with heterocyclic groups;
  - (c) one or more antioxidants; and
  - (d) one or more colorants chosen from oxidative dye precursors, direct dyes, pigments, and mixtures thereof; and
- (2) a second unit containing an oxidizing composition comprising: (i) one or more oxidizing agents chosen from peroxides, persulfates, perborates, percarbonates, alkali metal bromates, ferricyanides, laccases, peroxidases, redox enzymes, their salts thereof, and mixtures thereof, and (ii) a cosmetically acceptable solvent selected from water and a water/organic solvent mixture;
  - wherein the one or more divalent metal salts of an inorganic acid, the one or more monovalent or divalent metal salts of an organic acid, the one or more antioxidants, and the one or more colorants of the first unit are contained in one or more separate containers.

23. The multi-compartment kit of claim 22, wherein:
the one or more divalent metal salts of an inorganic acid and the one or more monovalent or divalent metal salts of an organic acid are contained in a first container; the one or more antioxidants are contained in a second container; and the one or more colorants are contained in a third container; or
the one or more divalent metal salts of an inorganic acid, the one or more monovalent or divalent metal salts of an organic acid, and the one or more antioxidants are contained in one container; and the one or more colorants are contained in another container.

* * * * *